(12) United States Patent
Yang et al.

(10) Patent No.: US 8,367,853 B2
(45) Date of Patent: Feb. 5, 2013

(54) METHOD AND SYSTEM FOR FORMING A PRECURSOR COMPOUND FOR NON-BRIDGED UNSYMMETRIC POLYOLEFIN POLYMERIZATION CATALYST

(75) Inventors: Qing Yang, Bartlesville, OK (US); Rex E. Murray, Bartlesville, OK (US); Richard M. Buck, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 13/186,237

(22) Filed: Jul. 19, 2011

(65) Prior Publication Data

US 2011/0275848 A1 Nov. 10, 2011

Related U.S. Application Data

(62) Division of application No. 12/466,229, filed on May 14, 2009, now Pat. No. 8,013,177.

(51) Int. Cl.
*C07F 7/00* (2006.01)
*C08F 4/76* (2006.01)

(52) U.S. Cl. ............ 556/52; 556/51; 502/113; 526/170; 526/943; 526/941

(58) Field of Classification Search .................... 556/53, 556/52, 51; 526/160, 170, 943
See application file for complete search history.

(56) References Cited

U.S. PATENT DOCUMENTS

| | | | |
|---|---|---|---|
| 3,248,179 A | 4/1966 | Norwood | |
| 4,501,885 A | 2/1985 | Sherk et al. | |
| 4,588,790 A | 5/1986 | Jenkins et al. | |
| 5,352,749 A | 10/1994 | DeChellis et al. | |
| 5,436,304 A | 7/1995 | Griffin et al. | |
| 5,455,314 A | 10/1995 | Burns et al. | |
| 5,565,175 A | 10/1996 | Burns et al. | |
| 5,575,979 A | 11/1996 | Hanson | |
| 5,866,497 A | 2/1999 | Murray et al. | |
| 6,239,235 B1 | 5/2001 | Hottovy et al. | |
| 6,262,191 B1 | 7/2001 | Hottovy et al. | |
| 6,440,889 B1 * | 8/2002 | Tsuie ............................ | 502/152 |
| 6,531,619 B1 | 3/2003 | Gately et al. | |
| 6,833,415 B2 | 12/2004 | Kendrick et al. | |
| 7,064,225 B2 | 6/2006 | Thorn et al. | |
| 7,226,886 B2 | 6/2007 | Jayaratne et al. | |
| 7,439,379 B2 | 10/2008 | Hanaoka et al. | |
| 2007/0060722 A1 | 3/2007 | Jayaratne et al. | |

FOREIGN PATENT DOCUMENTS

JP 2000-256413 A1 9/2000
WO WO 2007-055978 A1 5/2007

OTHER PUBLICATIONS

Ready et al., J. Organomet. Chem., 1999, 583, 11-27.*
Rogers et al., Organometallics, 1999, 3976-3980.*
Alt et al., Inorg. Chim. Acta, 2003, 343, 253-274.*
Alt, Helmut G., et al., "Bridged and unbridged substituted indenyl complexes of titanium and zirconium as catalysts for homogeneous and heterogeneous homo- and copolymerization of olefins," Inorganica Chimica Acta, vol. 343, Jan. 30, 2003, pp. 253-274.
Buck, Richard M., PI: "Synthesis of Unsymmetric Metallocenes using Mixed Amido-Chloro Precursors", Experimental Section, Version 1, 2008, pp. 1-4.
Cano Sierra, Jesus, et al., "Formation of Dinuclear Titanium and Zirconium Complexes by Olefin Metathesis-Catalytic Preparation of Organometallic Catalyst Systems," Chemistry—A European Journal, Wiley-V C H Verlag GMBH & Co. KGAA, Weinheim, DE., vol. 9, No. 15, Aug. 4, 2003, pp. 3618-3622.
Diamond, Gary M. et al., Efficient Synthesis of Chiral ansa-Metallocenes by Amine Elimination. Synthesis, Structure, and Reactivity of rac-(EBI)Zr(NMe2)2, J. Am. Chem. Soc., 1996, pp. 8024-8033, vol. 118.
Diamond, Gary M. et al., Efficient Synthesis of rac-(Ethylenebis(indenyl))ZrX2 Complexes via Amine Elimination, Organometallics, 1995, pp. 5-7, vol. 14.
Morris, Robert J. et al., Di-u-chloro-bis[chloro(n5-indenyl)methylhafnium(IV)], Acta Crystallographica Section C, 1998, pp. 1617-1618, vol. C54.
Morris, Robert J. et al., Monoindenyltrichloride Complexes of Titanium(IV), Zirconium(IV), and Hafnium(IV), Transition Metal Complexes and Precursors, Inorganic Synthesis, vol. 32, Jan. 5, 2007, p. 215-221.
Morris, Robert J. et al., The Preparation and variable temperature 1H NMR characterization of 1-(tri-n-butylstannyl) indene, 1-(Bu3Sn)C9H7, Polyhedron, 1997, pp. 3699-3704, vol. 16, No. 21.
Ready, Thomas E., et al., "New indenyl titanium catalysts for syndiospecific styrene polymerizations," Journal of Organometallic Chemistry, vol. 583, Sep. 30, 1999, pp. 11/27.
Rogers, et al., Organometallics, 1999 18, 3976-3980.
Shaw, Scott L. et al., Monoidenyl titanium alkyl halides. The synthesis and molecular structures of (n5-C9H7)TiBr3, (n5-C9H7)Ti(CH3)Br2, and (n5-C9H7)Ti(CH3)Cl2, Inorganica Chimica Acta, 1999, pp. 220-224, vol. 292.
Shaw, Scott L. et al., Monoindenyl halides of zirconium and hafnium. The preparation of [n5-C9H7)zrCl3]n and [(n5-C9H7)HfCl2(u-Cl)]2 and the crystal structure of [(n5-C9H7)HfCl2(u-Cl)]2, Journal of Organometallic Chemistry, 1995, pp. C4-C6.
International Patent Application No. PCT/US2010/001426 Search Report (Jan. 31, 2011).

* cited by examiner

*Primary Examiner* — Rip A. Lee
(74) *Attorney, Agent, or Firm* — Fletcher Yoder

(57) ABSTRACT

The present techniques relates generally to polyolefin catalysts and, more specifically, to preparing a precursor compound for an unsymmetric metallocene catalyst, for using the precursor compound to prepare catalysts, and for employing the precursor compounds to prepare catalysts for polyolefin polymerizations.

20 Claims, 5 Drawing Sheets

METHOD AND SYSTEM FOR FORMING A PRECURSOR COMPOUND FOR NON-BRIDGED UNSYMMETRIC POLYOLEFIN POLYMERIZATION CATALYST

CROSS-REFERENCE TO RELATED APPLICATIONS

This application is a divisional of U.S. patent application Ser. No. 12/466,229, now U.S. Pat. No. 8,013,177, entitled "METHOD AND SYSTEM FOR FORMING A PRECURSOR COMPOUND FOR NON-BRIDGED UNSYMMETRIC POLYOLEFIN POLYMERIZATION CATALYST" filed on May 14, 2009, which is incorporated by reference herein in its entirety.

BACKGROUND

The present techniques relate generally to polyolefin catalysts and, more specifically, to preparing a precursor compound for an unsymmetric metallocene catalyst, for using the precursor compound to prepare catalysts, and for employing the precursor compounds to prepare catalysts for polyolefin polymerizations.

This section is intended to introduce the reader to aspects of art that may be related to aspects of the present techniques, which are described and/or claimed below. This discussion is believed to be helpful in providing the reader with background information to facilitate a better understanding of the various aspects of the present techniques. Accordingly, it should be understood that these statements are to be read in this light, and not as admissions of prior art.

As chemical and petrochemical technologies have advanced, the products of these technologies have become increasingly prevalent in society. In particular, as techniques for bonding simple molecular building blocks into longer chains (or polymers) have advanced, the polymer products, typically in the form of various plastics, have been increasingly incorporated into various everyday items. For example, polyolefin polymers, such as polyethylene, polypropylene, and their copolymers, are used for retail and pharmaceutical packaging, food and beverage packaging (such as juice and milk bottles), household containers (such as pails and boxes), household items (such as appliances, furniture, carpeting, and toys), automobile components, pipes, conduits, and various industrial products.

Specific types of polyolefins, such as high-density polyethylene (HDPE), have particular applications in the manufacture of blow-molded and injection-molded goods, such as food and beverage containers, film, and plastic pipe. Other types of polyolefins, such as low-density polyethylene (LDPE), linear low-density polyethylene (LLDPE), isotactic polypropylene (iPP), and syndiotactic polypropylene (sPP) are also suited for similar applications. The mechanical requirements of the application, such as tensile strength and density, and/or the chemical requirements, such thermal stability, molecular weight, and chemical reactivity, typically determine what polyolefin or type of polyolefin is suitable.

To achieve these properties, various combinations of reaction systems may be used. For example, to form lower density products, such as LDPE and LLDPE, among others, two monomers may be polymerized together, i.e., co-polymerized. This forms a polymer that is described as having "short-chain branching." Other polymers may have links between chains formed, called "long-chain branching," while yet other polymers may have minimal branching of either type. Favorable properties may be obtained for polymers that are formed as in-situ blends of these types of branched polymer chains, such as in a single reactor using two different catalysts. The properties obtained for these blends may be determined by the molecular weights of each of the polymers and by which polymer is branched, e.g., short or long chains, among others. To obtain polymers having high strength and ease of processability, the branching should generally be confined to the higher molecular weight polymer. Accordingly, continuing efforts in catalyst research are directed towards developing mixed catalyst systems that may be used to form in-situ polymer blends, as well as more efficient ways of making these mixed catalyst systems.

DETAILED DESCRIPTION OF SPECIFIC EMBODIMENTS

Figure 1:
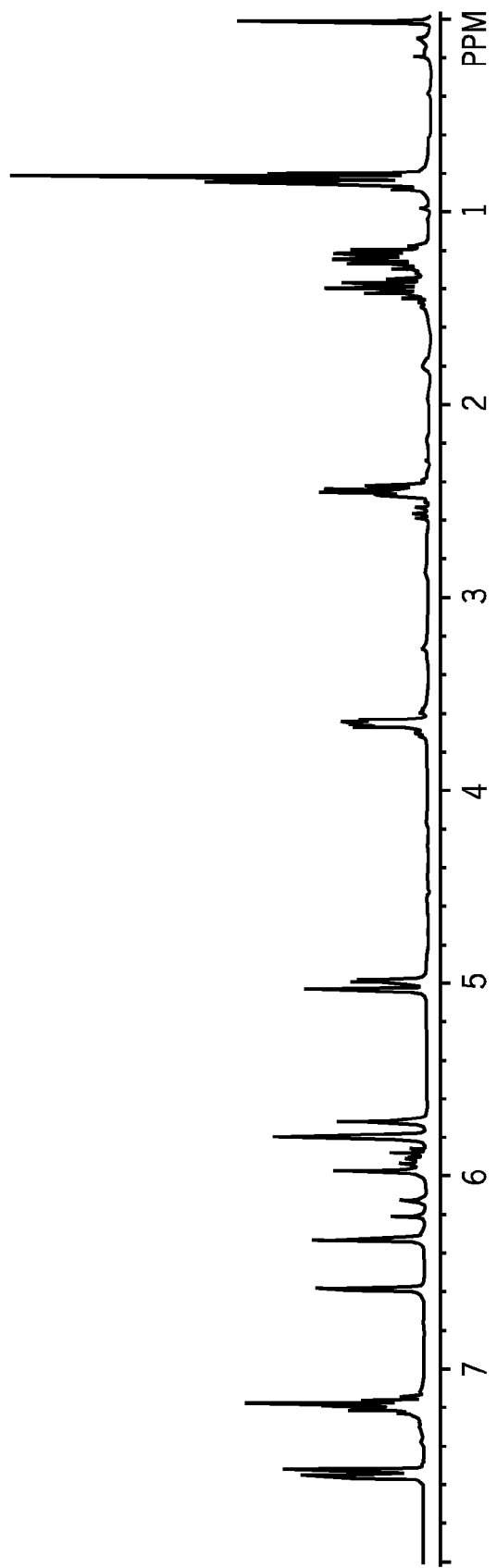
FIG. 1 is an $^1$H-NMR (CDCl$_3$) spectrum of Example Reaction 1 in accordance with embodiments of the present techniques.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Molecular weight is an important factor that affects the final properties of a polyolefin. Control of molecular weight may be used to create polyolefin resins that are strong, chemically resistant, and yet easily processed in extrusion machines. One way that molecular weight may be controlled to obtain desirable properties for a polyolefin resin is through the synthesis of bimodal polyolefin resins, i.e., in-situ resin blends that combine resins from two distinct molecular weight regions. For example, a high molecular weight resin may provide the bimodal polyolefin with strength and chemical resistance, while a low molecular weight resin may provide the bimodal polyolefin with good processability. As resins that have substantial differences in molecular weight are generally not easy to blend, such resins may be created by forming the two molecular weight resins during a single reaction or reaction sequence. This may be performed in a single reactor or in sequential reactors.

Another important factor controlling the properties of a final resin is branching. Branching may take the form of branch points where new polymer chains grow, termed "long chain branching," or may be points where carbon chains having double bonds as end groups (comonomers) are incorporated into the polymer backbone, which is termed "short chain branching." Short chain branching may be controlled by the concentration of comonomers added to the polymerization reaction. The comonomers are randomly incorporated into the polymer backbone, and provide sites where the chains may leave a crystallite and join in adjacent crystallites. Generally, in a bimodal polymer, more favorable properties are achieved if the high molecular weight portion has a significant proportion of the short-chain branching, while the low molecular weight portion has much less short chain branching. To achieve this, catalyst systems have been developed that both form short molecular weight chains, and also do not significantly incorporate comonomer.

The present techniques are directed to catalyst precursors, methods for making the catalyst precursors, and methods for using the catalyst precursors to manufacture products made from polyolefins. More specifically, the present techniques disclose alkenyl substituted indenyl complexes that may be used as catalyst precursors. The catalyst precursors may be used to form metallocene catalysts capable of forming the low molecular weight polyolefin portion in a bimodal polyolefin. Further, these catalysts may be used with bridged metallocene catalysts that generally form high molecular weight polyolefins to prepare mixed catalyst systems that are capable of forming bimodal polymers.

An example of an unbridged metallocene catalyst that may be used to prepare the low molecular weight portion of a bimodal catalyst is shown in the structure illustrated in EQN. 1, below.

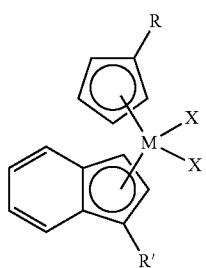

EQN. 1

In EQN. 1, R and R' are generally straight chains of 4 to 10 carbons and may be aliphatic or may have an olefinic (double bond) end group. X is a halogen ion, such as F, Cl, Br or I (generally Cl), and M is a group IV metal, such as Ti, Zr, or Hf (generally Zr).

The catalyst structure illustrated in EQN. 1 may generally be prepared by reaction schemes similar to those illustrated in EQN. 2, below.

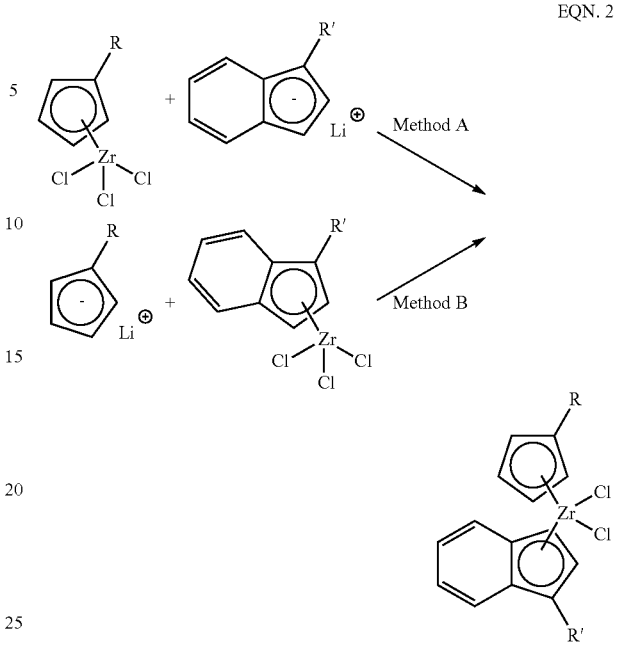

EQN. 2

Method A involves the synthesis and purification of $RCpZrCl_3$ prior to the synthesis of the catalyst. However, when R is a straight chain aliphatic or olefinic chain, the resulting compound may be an oil or tar that may be difficult to purify. Further, Method B generally involves the use of tin compounds as intermediates in the synthesis of the corresponding zirconium trichloride species, which may be difficult to remove after the synthesis. Accordingly, new techniques for synthesizing these compounds may be desirable.

Techniques for forming these catalysts from new catalyst precursors are disclosed herein. The synthesis techniques are based on reactions of allyl-indenyl compounds with metal complexes containing amido or mixed-amido/chloro ligands. The catalyst precursors have the general formula shown in EQN. 3, below.

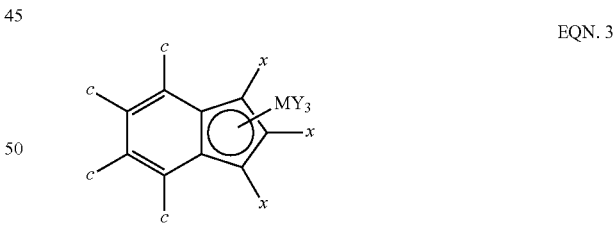

EQN. 3

In EQN. 3, M may be Ti, Zr, or Hf. Each x may independently be a hydrogen, alkyl, branched alkyl, cycloalkyl, aryl, or alkenyl group having from 2 to 20 carbons. At least one x is the alkenyl group having from 2 to 20 carbons where the alkenyl group is a terminal alkenyl group, internal alkenyl group (e.g. having cis or trans stereochemistry), or a branched alkenyl group (e.g., having Z or E stereochemistry). In certain embodiments, the alkenyl group may have additional functionality, such as aromatic, halogen, or silyl moieties. Each Y may independently be a halide or $NR_2$, where each R may independently be a hydrocarbyl group having from 1 to 5 carbons. Each c may independently be a hydrogen, alkyl, branched alkyl, cycloalkyl, aryl, or alkenyl group having from 2 to 20 carbons. Moreover, in certain embodiments two c groups may be conjoined to form a ring. In an embodiment, for example, the new precursor compound may have the general formula shown in EQN. 4.

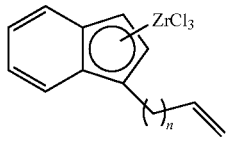

EQN. 4

In EQN. 4, n may be 1, 2, 3, 4, 5, 6, 7, or 8. In another embodiment, the precursor compound may have the general formula shown in EQN. 5.

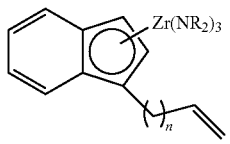

EQN. 5

In EQN. 5, n may be 1, 2, 3, 4, 5, 6, 7, or 8, and R may be defined as above. The ligands on the precursor compound do not have to be identical, as they may be any combination of halo and amido groups, as illustrated by the embodiment shown in EQN. 6.

EQN. 6

In EQN. 6, n and R are defined as above.

A general reaction scheme to form the precursor compounds and then use the precursor compounds to form the catalyst is shown in EQN. 7.

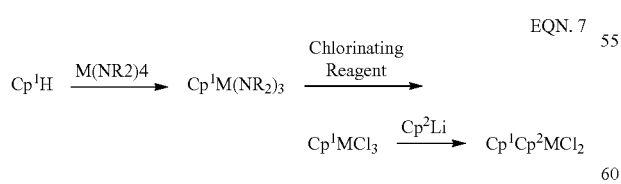

EQN. 7

In EQN. 7, $Cp^1$ is generally a substituted indenyl and $Cp^1$ may be a substituted cyclopentadienyl, a substituted indenyl, or a substituted fluorenyl. M may be Ti, Zr, or Hf, and the chlorinating reagent may be HCl, $Me_2NH/HCl$, or $Me_3SiCl$, among others. One embodiment of this reaction scheme is shown in EQN. 8.

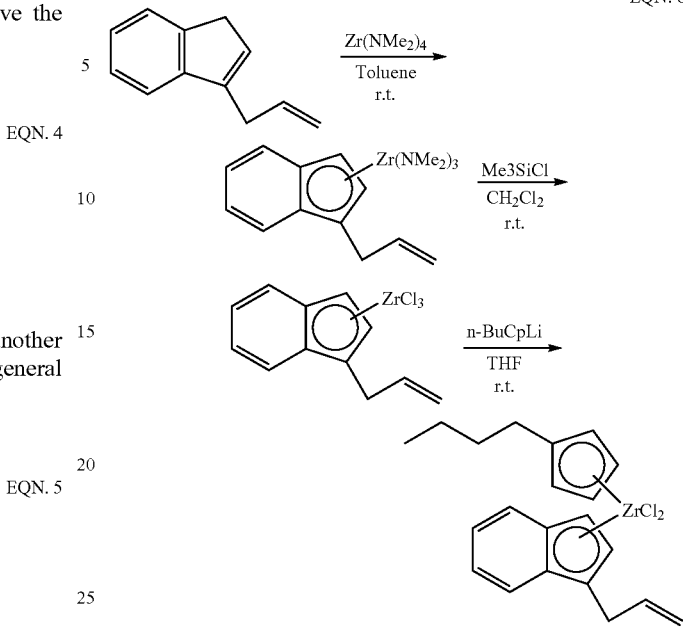

EQN. 8

Another general technique that may be used to form the catalyst precursor uses organolithium compounds. An example of this technique in forming the catalyst precursor, and from that the catalyst, is shown in the reaction sequence in EQN. 9.

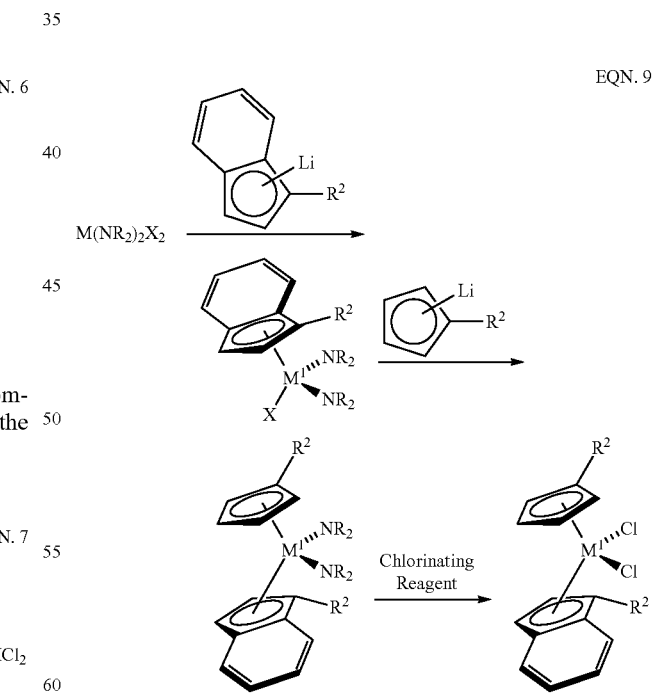

EQN. 9

In EQN. 9, M may be Ti, Zr, or Hf. R may be any alkyl having 1 to 10 carbons, and $R^2$ may be a carbon chain having 4 to 10 carbons and a double bond between the last two carbons. In a further technique, the reaction sequence can be carried out in a one-pot reaction as shown in Eqn 10.

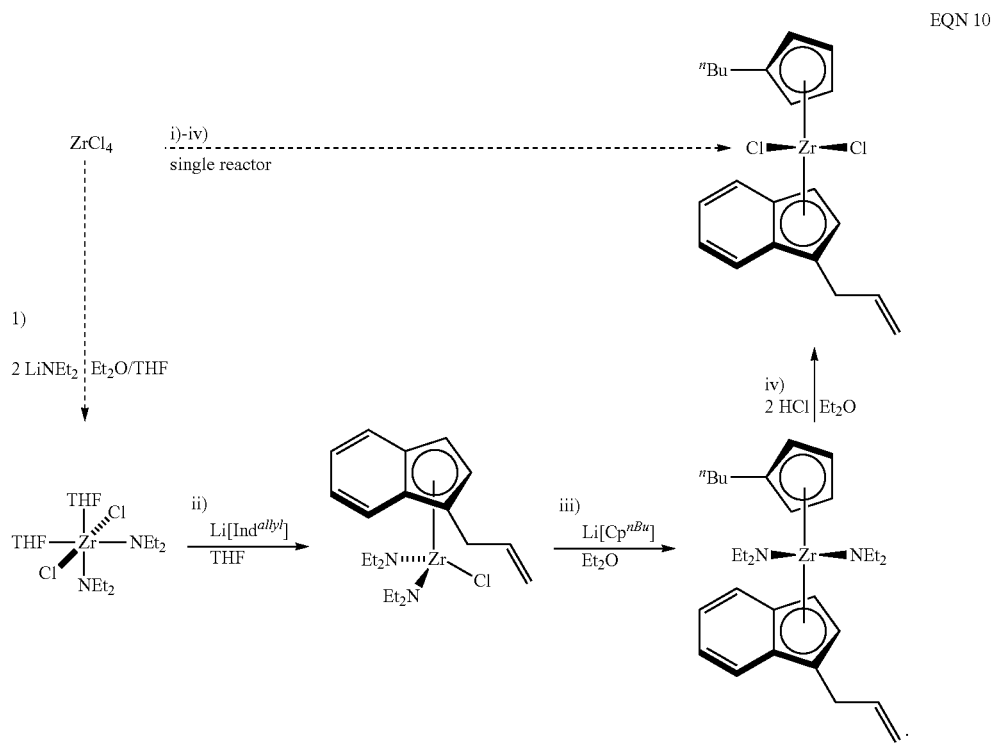

EQN 10

A final technique that may be used to make the catalyst precursor is shown in EQN. 11.

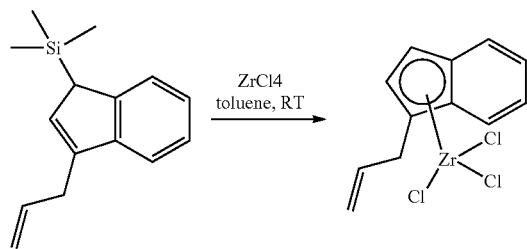

EQN. 11

Components that May be Used to Form Polymerization Reaction Mixtures

The catalyst systems of the present techniques may include the unbridged metallocene catalysts disclosed herein, and may also include a tightly-bridged ansa-metallocene compound that has an alkyl or alkenyl group of three to 20 carbons bonded to a $\eta^5$-cyclopentadienyl-type ligand (such as, for example, a cyclopentadienyl, an indenyl, or a fluorenyl). A general description of the ansa-metallocene complex is presented in the following subsection. The subsections that follow after that discuss other components that may generally be present in an active olefin polymerization, including the solid oxide support/activator, the aluminum cocatalyst, and a monomer/comonomer.

A. Tightly Bridged Metallocene Catalysts

The tightly bridged metallocene compound may be useful for generating the higher molecular weight segment with reasonable comonomer incorporate, as discussed herein. Generally, the term "bridged" or "ansa-metallocene" refers to a metallocene compound in which the two $\eta^5$-cycloalkadienyl-type ligands in the molecule are linked by a bridging moiety. Useful ansa-metallocenes may be "tightly-bridged," meaning that the two $\eta^5$-cycloalkadienyl-type ligands are connected by a bridging group wherein the shortest link of the bridging moiety between the $\eta^5$-cycloalkadienyl-type ligands is a single atom. The metallocenes described herein are therefore bridged bis($\eta^5$-cycloalkadienyl)-type compounds. The bridging group may have the formula $>ER^1R^2$, wherein E may be a carbon atom, a silicon atom, a germanium atom, or a tin atom, and wherein E is bonded to both $\eta^5$-cyclopentadienyl-type ligands. In this embodiment, $R^1$ and $R^2$ may be independently an alkyl group or an aryl group, either of which having up to 12 carbon atoms, or hydrogen.

In embodiments of the present techniques, the ansa-metallocene of the present techniques may be expressed by the general formula:

$$(X^1)(X^2)(X^3)(X^4)M^1.$$

In this formula, $M^1$ may be titanium, zirconium, or hafnium, $X^1$ may be a substituted cyclopentadienyl, a substituted indenyl, or a substituted fluorenyl. $X^2$ may be a substituted cyclopentadienyl or a substituted fluorenyl. One substituent on $X^1$ and $X^2$ is a bridging group having the formula $ER^1R^2$. E may be a carbon atom, a silicon atom, a germanium atom, or a tin atom, and is bonded to both $X^1$ and $X^2$. $R^1$ and $R^2$ may be independently an alkyl group or an aryl group, either of which may have up to 12 carbon atoms, or may be hydrogen. The bridging groups may be selected to influence the activity of the catalyst or the structure of the polymer produced. One substituent on $X^2$ may be a substituted or an unsubstituted alkyl or alkenyl group, which may have up to 12 carbon atoms. Substituents $X^3$ and $X^4$ may be independently: 1) F, Cl, Br, or I; 2) a hydrocarbyl group having up to 20 carbon atoms, H, or $BH_4$; 3) a hydrocarbyloxide group, a hydrocarbylamino group, or a trihydrocarbylsilyl group, any of which may have up to 20 carbon atoms; 4) $OBR^A{}_2$ or $SO_3R^A$, wherein $R^A$ may be an alkyl group or an aryl group, either of which may have up to 12 carbon atoms. Any additional substituent on the substituted cyclopentadienyl, substituted indenyl, substituted fluorenyl, or substituted alkyl group may be independently an aliphatic group, an aromatic group, a cyclic group, a combination of aliphatic and cyclic groups, an oxygen group, a sulfur group, a nitrogen group, a phosphorus group, an arsenic group, a carbon group, a silicon group, or a boron group, any of which may have from 1 to 20 carbon atoms. Alternatively, additional substituents may be present, including halides or hydrogen. The substituents on the $\eta^5$-cyclopentadienyl-type ligands may be used to control the activity of the catalyst or the stereochemistry of the polymer produced.

An example of an ansa-metallocene that may be used in embodiments is presented in EQN. 12, below.

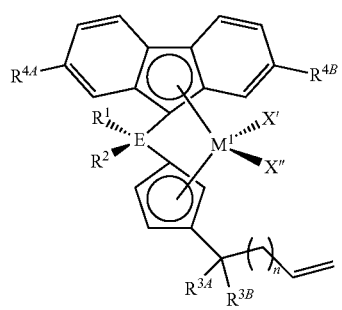

EQN. 12

In EQN. n, $M^1$ may be zirconium or hafnium and X' and X" may be independently F, Cl, Br, or I. E may be C or Si and $R^1$ and $R^2$ may be independently an alkyl group or an aryl group, either of which may have up to 10 carbon atoms, or $R^1$ and $R^2$ may be hydrogen. $R^{3A}$ and $R^{3B}$ may be independently a hydrocarbyl group or a trihydrocarbylsilyl group, any of which may have up to 20 carbon atoms, or may be hydrogen. The subscript 'n' may be an integer that may range from 0 to 10, inclusive. $R^{4A}$ and $R^{4B}$ may be independently a hydrocarbyl group that may have up to 12 carbon atoms, or may be hydrogen.

However, the catalyst systems of the present disclosure are not limited to the bridged metallocenes shown above. Indeed, any bridged or unbridged metallocene that forms high molecular weight copolymers with good comonomer incorporation may be used instead.

B. Solid Oxide Activator/Support

The present techniques encompass catalyst compositions that include an acidic activator-support, such as, for example, a chemically-treated solid oxide (CTSO). A CTSO may be used in combination with an organoaluminum compound. The activator-support may include a solid oxide treated with an electron-withdrawing anion. The solid oxide may include such compounds as silica, alumina, silica-alumina, aluminophosphate, aluminum phosphate, zinc aluminate, heteropolytungstates, titania, zirconia, magnesia, boria, zinc oxide, mixed oxides thereof, and the like, or any mixture or combination thereof. The electron-withdrawing anion may include fluoride, chloride, bromide, iodide, phosphate, triflate, bisulfate, sulfate, sulfite, fluoroborate, fluorosulfate, trifluoroacetate, phosphate, fluorophosphate, fluorozirconate, fluorosilicate, fluorotitanate, permanganate, substituted or unsubstituted alkanesulfonate, substituted or unsubstituted arenesulfonate, substituted or unsubstituted alkylsulfate, or any combination thereof.

The activator-support may include the contact product of the solid oxide compound and the electron-withdrawing anion source. Further, the solid oxide compound may include an inorganic oxide and may be optionally calcined prior to contacting the electron-withdrawing anion source. The contact product may also be calcined either during or after the solid oxide compound is contacted with the electron-withdrawing anion source. In this embodiment, the solid oxide compound may be calcined or uncalcined. The activator-support may also include the contact product of a calcined solid oxide compound and an electron-withdrawing anion source.

The solid oxide is not necessarily limited to the compounds discussed above. Any number of other compounds, including oxides of zinc, nickel, vanadium, silver, copper, gallium, tin, tungsten, molybdenum, or any combinations thereof, may be used. Examples of activator-supports that further include an additional metal or metal ion include, for example, chlorided zinc-impregnated alumina, fluorided zinc-impregnated alumina, chlorided vanadium-impregnated alumina, fluorided zinc-impregnated silica-alumina, chlorided nickel-impregnated alumina, or any combinations thereof. Further, other compounds may be used in addition to or in place of the solid oxide, such as borates, ionizing ionic compounds, and the like.

C. Organoaluminum Compounds

The catalyst systems may include the unbridged metallocene catalysts of the present disclosure, a tightly-bridged ansa-metallocene compound having an alkyl or alkenyl moiety bonded to a $\eta^5$-cyclopentadienyl-type ligand, a solid oxide activator-support, and, an organoaluminum compound. The organoaluminum compound may be omitted when it is not needed to impart catalytic activity to the catalyst composition.

Organoaluminum compounds that may be used in the catalyst systems include, for example, compounds with the formula:

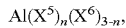

$Al(X^5)_n(X^6)_{3-n}$, wherein $X^5$ may be a hydrocarbyl having from 1 to about 20 carbon atoms; $X^6$ may be alkoxide or aryloxide, any of which having from 1 to about 20 carbon atoms, halide, or hydride; and n may be a number from 1 to 3, inclusive. In various embodiments, $X^5$ may be an alkyl having from 1 to about 10 carbon atoms. Moieties used for $X^5$ may include, for example, methyl, ethyl, propyl, butyl, sec-butyl, isobutyl, 1-hexyl, 2-hexyl, 3-hexyl, isohexyl, heptyl, or octyl, and the like. In other embodiments, $X^6$ may be independently fluoride, chloride, bromide, methoxide, ethoxide, or hydride. In yet another embodiment, $X^6$ may be chloride.

In the formula $Al(X^5)_n(X^6)_{3-n}$, n may be a number from 1 to 3 inclusive, and in an exemplary embodiment, n is 3. The value of n is not restricted to an integer, therefore this formula may include sesquihalide compounds, other organoaluminum cluster compounds, and the like.

Generally, organoaluminum compounds that may be used in the catalyst systems may include trialkylaluminum compounds, dialkylaluminium halide compounds, dialkylaluminum alkoxide compounds, dialkylaluminum hydride compounds, and combinations thereof. Examples of such organoaluminum compounds include trimethylaluminum, triethylaluminum (TEA), tripropylaluminum, tributylaluminum, tri-n-butylaluminum (TNBA), triisobutylaluminum (TIBA), trihexylaluminum, triisohexylaluminum, trioctylaluminum, diethylaluminum ethoxide, diisobutylaluminum hydride, or diethylaluminum chloride, or any combination thereof. If the particular alkyl isomer is not specified, the compound may encompass all isomers that can arise from a particular specified alkyl group.

D. The Olefin Monomer

In the present techniques, various unsaturated reactants may be useful in the polymerization processes with catalyst compositions and processes. Such reactants include olefin compounds having from about 2 to about 30 carbon atoms per molecule and having an olefinic double bond. The present techniques encompass homopolymerization processes using a single olefin such as ethylene or propylene, as well as copolymerization reactions with two or more different olefinic compounds. For example, in a copolymerization reaction with ethylene, copolymers may include a major amount of ethylene (>50 mole percent) and a minor amount of comonomer <50 mole percent. The comonomers that may be copolymerized with ethylene may have from three to about 20 carbon atoms in their molecular chain.

Olefins that may be used as monomer or comonomer include acyclic, cyclic, polycyclic, terminal ($\alpha$), internal, linear, branched, substituted, unsubstituted, functionalized, and non-functionalized olefins. For example, compounds that may be polymerized with the catalysts of the present techniques include propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-hexene, 3-ethyl-1-hexene, 1-heptene, 2-heptene, 3-heptene, the four normal octenes, the four normal nonenes, the five normal decenes, or any combination thereof. Further, cyclic and bicyclic olefins, including, for example, cyclopentene, cyclohexene, norbornylene, norbornadiene, and the like, may also be polymerized as described above.

The amount of comonomer introduced into a reactor zone to produce a copolymer may be from about 0.001 to about 99 weight percent comonomer based on the total weight of the monomer and comonomer, generally from about 0.01 to about 50 weight percent. In other embodiments, the amount of comonomer introduced into a reactor zone may be from about 0.01 to about 10 weight percent comonomer or from about 0.1 to about 5 weight percent comonomer. Alternatively, an amount sufficient to give the above described concentrations, by weight, of the copolymer produced, may be used.

While not intending to be bound by theory, it is believed that steric hindrance can impede or slow the polymerization process if branched, substituted, or functionalized olefins are used as reactants. However, if the branched and/or cyclic portion(s) of the olefin are somewhat removed from the carbon-carbon double bond they would not be expected to hinder the reaction as much as more proximate substituents.

In exemplary embodiments, a reactant for the catalyst compositions of the present techniques is ethylene, so the polymerizations may be either homopolymerizations or copolymerizations with a different acyclic, cyclic, terminal, internal, linear, branched, substituted, or unsubstituted olefin. In addition, the catalyst compositions of the present techniques may be used in polymerization of diolefin compounds, including for example, such compounds as 1,3-butadiene, isoprene, 1,4-pentadiene, and 1,5-hexadiene.

Use of the Catalyst System in Polymerization Processes

The catalysts of the present techniques are intended for any olefin polymerization method, using various types of polymerization reactors. As used herein, "polymerization reactor" includes any polymerization reactor capable of polymerizing olefin monomers to produce homopolymers or copolymers. Such homopolymers and copolymers may be referred to as resins or polymers. The various types of reactors include those that may be referred to as batch, slurry, gas-phase, solution, high pressure, tubular or autoclave reactors. Gas phase reactors may include fluidized bed reactors or staged horizontal reactors. Slurry reactors may include vertical or horizontal loops. High pressure reactors may include autoclave or tubular reactors. Reactor types may include batch or continuous processes. Continuous processes could use intermittent or continuous product discharge. Processes may also include partial or full direct recycle of un-reacted monomer, un-reacted comonomer, and/or diluent.

Polymerization reactor systems of the present techniques may include one type of reactor in a system or multiple reactors of the same or different type. Production of polymers in multiple reactors may include several stages in at least two separate polymerization reactors interconnected by a transfer device making it possible to transfer the polymers resulting from the first polymerization reactor into the second reactor. The desired polymerization conditions in one of the reactors may be different from the operating conditions of the other reactors. Alternatively, polymerization in multiple reactors may include the manual transfer of polymer from one reactor to subsequent reactors for continued polymerization. Multiple reactor systems may include any combination including, but not limited to, multiple loop reactors, multiple gas reactors, a combination of loop and gas reactors, multiple high pressure reactors or a combination of high pressure with loop and/or gas reactors. The multiple reactors may be operated in series or in parallel.

A. Loop Slurry Polymerization Processes

In embodiments of the present techniques, the polymerization reactor system may include a loop slurry reactor. Such reactors may include vertical or horizontal loops. Monomer, diluent, catalyst and optionally any comonomer may be continuously fed to the loop reactor where polymerization occurs. Generally, continuous processes may include the continuous introduction of a monomer, a catalyst, and a diluent into a polymerization reactor and the continuous removal from this reactor of a suspension including polymer particles and the diluent. Reactor effluent may be flashed to remove the solid polymer from the liquids that include the diluent, monomer and/or comonomer. Various technologies may be employed for this separation step including but not limited to, flashing that may include any combination of heat addition and pressure reduction; separation by cyclonic action in either a cyclone or hydrocyclone; or separation by centrifugation.

Loop slurry polymerization processes (also known as the particle form process) are disclosed, for example, in U.S. Pat. Nos. 3,248,179, 4,501,885, 5,565,175, 5,575,979, 6,239,235, 6,262,191 and 6,833,415, each of which is incorporated by reference in its entirety herein. If any definitions, terms, or descriptions used in any of these references conflicts with the usage herein, the usage herein takes precedence over that of the reference.

Diluents that may be used in slurry polymerization include, for example, the monomer being polymerized and hydrocarbons that are liquids under reaction conditions. Examples of such diluents may include, for example, hydrocarbons such as propane, cyclohexane, isobutane, n-butane, n-pentane, isopentane, neopentane, and n-hexane. Some loop polymerization reactions can occur under bulk conditions where no diluent may be used or where the monomer (e.g., propylene) acts as the diluent. An example is polymerization of propylene monomer as disclosed in U.S. Pat. No. 5,455,314, which is incorporated by reference in its entirety herein.

B. Gas Phase Polymerization Processes

Further, the polymerization reactor may include a gas phase reactor. Such systems may employ a continuous recycle stream containing one or more monomers continuously cycled through a fluidized bed in the presence of the catalyst under polymerization conditions. A recycle stream may be withdrawn from the fluidized bed and recycled back into the reactor. Simultaneously, polymer product may be withdrawn from the reactor and new or fresh monomer may be added to replace the polymerized monomer. Such gas phase reactors may include a process for multi-step gas-phase polymerization of olefins, in which olefins are polymerized in the gaseous phase in at least two independent gas-phase polymerization zones while feeding a catalyst-containing polymer formed in a first polymerization zone to a second polymerization zone. One type of gas phase reactor is disclosed in U.S. Pat. Nos. 5,352,749, 4588,790 and 5,436,304, each of which is incorporated by reference in its entirety herein.

According to still another aspect of the techniques, a high pressure polymerization reactor may include a tubular reactor or an autoclave reactor. Tubular reactors may have several zones where fresh monomer, initiators, or catalysts are added. Monomer may be entrained in an inert gaseous stream and introduced at one zone of the reactor. Initiators, catalysts, and/or catalyst components may be entrained in a gaseous stream and introduced at another zone of the reactor. The gas streams may be intermixed for polymerization. Heat and pressure may be employed appropriately to obtain optimal polymerization reaction conditions.

C. Solution Polymerization Processes

According to yet another aspect of the techniques, the polymerization reactor may include a solution polymerization reactor wherein the monomer is contacted with the catalyst composition by suitable stirring or other means. A carrier including an inert organic diluent or excess monomer may be employed. If desired, the monomer may be brought in the vapor phase into contact with the catalytic reaction product, in the presence or absence of liquid material. The polymerization zone may be maintained at temperatures and pressures that will result in the formation of a solution of the polymer in a reaction medium. Agitation may be employed to obtain better temperature control and to maintain uniform polymerization mixtures throughout the polymerization zone. Adequate means may be utilized for dissipating the exothermic heat of polymerization.

D. Reactor Support Systems

Polymerization reactors suitable for the present techniques may further include any combination of a raw material feed system, a feed system for catalyst or catalyst components, and/or a polymer recovery system. Such systems may include systems for feedstock purification, catalyst storage and preparation, extrusion, reactor cooling, polymer recovery, fractionation, recycle, storage, loadout, laboratory analysis, and process control, among others.

E. Polymerization Conditions

Conditions that may be controlled for polymerization efficiency and to provide resin properties include temperature, pressure and the concentrations of various reactants. Polymerization temperature can affect catalyst productivity, polymer molecular weight and molecular weight distribution. Suitable polymerization temperature may be any temperature below the de-polymerization temperature according to the Gibbs Free energy equation. Typically this includes from about 60° C. to about 280° C., for example, and from about 70° C. to about 110° C., depending upon the type of polymerization reactor.

Suitable pressures will also vary according to the reactor and polymerization type. The pressure for liquid phase polymerizations in a loop reactor is typically less than 1000 psig. Pressure for gas phase polymerization is usually at about 200-500 psig. High pressure polymerization in tubular or autoclave reactors is generally run at about 20,000 to 75,000 psig. Polymerization reactors may also be operated in a supercritical region occurring at generally higher temperatures and pressures. Operation above the critical point of a pressure/temperature diagram (supercritical phase) may offer advantages.

The concentration of various reactants may be controlled to produce resins with certain physical and mechanical properties. The proposed end-use product that will be formed by the resin and the method of forming that product determines the desired resin properties. Mechanical properties include tensile, flexural, impact, creep, stress relaxation and hardness tests. Physical properties include density, molecular weight, molecular weight distribution, melting temperature, glass transition temperature, temperature melt of crystallization, density, stereoregularity, crack growth, long chain branching and rheological measurements.

The concentrations of monomer, co-monomer, hydrogen, co-catalyst, modifiers, and electron donors may be important in producing these resin properties. Comonomer may be used to control product density. Hydrogen may be used to control product molecular weight. Co-catalysts may be used to alkylate, scavenge poisons and control molecular weight. Modifiers may be used to control product properties and electron donors affect stereoregularity. In addition, the concentration of poisons must be minimized since they impact the reactions and product properties.

Final Products Made from Polymers

The polymer or resin fluff from the reactor system may have additives and modifiers added to provide better processing during manufacturing and for desired properties in the end product. Additives include surface modifiers such as slip agents, antiblocks, tackifiers; antioxidants such as primary and secondary antioxidants; pigments; processing aids such as waxes/oils and fluoroelastomers; and special additives such as fire retardants, antistats, scavengers, absorbers, odor enhancers, and degradation agents. After the addition of the additives, the polymer or resin fluff may be extruded and formed into pellets for distribution to customers and formation into final end-products.

To form end-products or components from the pellets, the pellets are generally subjected to further processing, such as blow molding, injection molding, rotational molding, blown film, cast film, extrusion (e.g., sheet extrusion, pipe and corrugated extrusion, coating/lamination extrusion, etc.), and so on. Blow molding is a process used for producing hollow plastic parts. The process typically employs blow molding equipment, such as reciprocating screw machines, accumulator head machines, and so on. The blow molding process may be tailored to meet the customer's needs, and to manufacture products ranging from the plastic milk bottles to the automotive fuel tanks mentioned above. Similarly, in injection molding, products and components may be molded for a wide range of applications, including containers, food and chemical packaging, toys, automotive, crates, caps and closures, to name a few.

Profile extrusion processes may also be used. Polyethylene pipe, for example, may be extruded from polyethylene pellet resins and used in an assortment of applications due to its chemical resistance, relative ease of installation, durability and cost advantages, and the like. Indeed, plastic polyethylene piping has achieved significant use for water mains, gas distribution, storm and sanitary sewers, interior plumbing, electrical conduits, power and communications ducts, chilled water piping, and well casings, among others. In particular, high-density polyethylene (HDPE), which generally constitutes the largest volume of the polyolefin group of plastics used for pipe, is tough, abrasion-resistant and flexible (even at subfreezing temperatures). Furthermore, HDPE pipe may be used in small diameter tubing and in pipe up to more than 8 feet in diameter. In general, polyethylene pellets (resins) may be supplied for the pressure piping markets, such as in natural gas distribution, and for the non-pressure piping markets, such as for conduit and corrugated piping.

Rotational molding is a high-temperature, low-pressure process used to form hollow parts through the application of heat to biaxially-rotated molds. Polyethylene pellet resins generally applicable in this process are those resins that flow together in the absence of pressure when melted to form a bubble-free part. Resins, such as those produced by the catalyst compositions of the present techniques, may offer such flow characteristics, as well as a wide processing window. Furthermore, these polyethylene resins suitable for rotational molding may exhibit desirable low-temperature impact strength, good load-bearing properties, and good ultraviolet (UV) stability. Accordingly, applications for rotationally-molded polyolefin resins include agricultural tanks, industrial chemical tanks, potable water storage tanks, industrial waste containers, recreational equipment, marine products, plus many more.

Sheet extrusion is a technique for making flat plastic sheets from a variety of resins. The relatively thin gauge sheets are generally thermoformed into packaging applications such as drink cups, deli containers, produce trays, baby wipe containers and margarine tubs. Other markets for sheet extrusion of polyolefin include those that utilize relatively thicker sheets for industrial and recreational applications, such as truck bed liners, pallets, automotive dunnage, playground equipment, and boats. A third use for extruded sheet, for example, is in geomembranes, where flat-sheet polyethylene material may be welded into large containment systems for mining applications and municipal waste disposal.

The blown film process is a relatively diverse conversion system used for polyethylene. The American Society for Testing and Materials (ASTM) defines films as less than 0.254 millimeter (10 mils) in thickness. However, the blown film process can produce materials as thick as 0.5 millimeter (20 mils), and higher. Furthermore, blow molding in conjunction with monolayer and/or multilayer coextrusion technologies lays the groundwork for several applications. Advantageous properties of the blow molding products may include clarity, strength, tearability, optical properties, and toughness, to name a few. Applications may include food and retail packaging, industrial packaging, and non-packaging applications, such as agricultural films, hygiene film, and so forth.

The cast film process may differ from the blown film process through the fast quench and virtual unidirectional orientation capabilities. These characteristics allow a cast film line, for example, to operate at higher production rates while producing beneficial optics. Applications in food and retail packaging take advantage of these strengths. Finally, polyolefin pellets may also be supplied for the extrusion coating and lamination industry.

Ultimately, the products and components formed from polyolefin (e.g., polyethylene) pellets may be further processed and assembled for distribution and sale to the consumer. For example, a polyethylene milk bottle may be filled with milk for distribution to the consumer, or the fuel tank may be assembled into an automobile for distribution and sale to the consumer.

EXAMLPES

Reagents

Unless otherwise noted, all operations were performed under purified nitrogen or vacuum using standard Schlenk or glovebox techniques. Diethyl ether and THF were purchased anhydrous from Aldrich and used as received. Toluene and pentane were degassed and dried over activated alumina. Heptane (Fisher Scientific) was degassed, and stored over activated 13X molecular sieves under nitrogen. Tetrakis(dimethylamino)zirconium was purchased from Strem. Zirconium tetrachloride, zirconium tetrakis(diethylamide), and hydrogen chloride solution in diethyl ether (2.0 M) were purchased from Sigma-Aldrich and used as received. Celite (Celite 545, Sigma-Aldrich) was dried for several days at 90-100° C. prior to use. $C_6D_6$ (Cambridge Isotope Laboratories) was stored over activated 13X molecular sieves under nitrogen. All other reagents not specified above were obtained from Aldrich Chemical Company and used without further purification. Li[$C_5H_4$—{$(CH_2)_3CH_3$}] was prepared by the reaction of n-butylcyclopentadiene with an equimolar amount of n-butyl lithium (Sigma-Aldrich, 2.5 M in hexanes) in diethyl ether. Li[$C_9H_6$-1-($CH_2CH=CH_2$)] was prepared by the reaction of 1-(prop-1-en-3-yl)indene with an equimolar amount of n-butyl lithium (Sigma-Aldrich, 2.5 M in hexanes) in heptane. NMR spectra were recorded using capped NMR tubes at ambient probe temperature. $^1H$ and $^{13}C$ chemical shifts are reported versus $SiMe_4$ and were determined by reference to the residual $^1H$ and $^{13}C$ solvent peaks. Coupling constants are reported in Hz.

Example 1

Preparation of (1-allylindenyl)(n-butylcyclopentadienyl)zirconium dichloride

To Tetrakis(dimethylamino)zirconium (0.52 g, 1.94 mmol) dissolved in toluene (9 mL) was added allylindene (0.31 g, 1.99 mmol) at room temperature. The mixture was stirred at room temperature overnight. Removal of the solvent gave an oil. To the oil was added $Me_3SiCl$ (7.5 mL of 1 M in methylene chloride, 7.5 mmol) at room temperature. The mixture was stirred at room temperature overnight. Removal of the solvent gave a yellow solid (crude allylindenylzirconium trichloride). The yellow solid (crude allylindenylzirconium trichloride) was dissolved in THF (10 mL). N-BuCpLi (0.273 g, 2.13 mmol) dissolved in THF (5 mL) was added to above THF solution (allylindenylzirconium trichloride/THF solution) at 0° C. The mixture was stirred at 0° C. for 30 minutes, then warned to room temperature and stirred for another 2.5 hours. The solvent was removed. The residue was extracted with toluene (30 mL). The supernatant was separated from the solid. Removal of the solvent gave a pale yellow solid. The pale yellow solid was washed with pentane (30 mL) and then dried under vacuum. The desired compound was obtained as a pale yellow solid (0.43 g, 51% overall yield). The product was identified by $^1H$-NMR (FIG. 1). The product was not further purified and contained small amount of impurity (bis(n-butylcyclopentadienyl)zirconium dichloride, about 6 mol % based on the integrals in $^1H$-NMR of the product).

Example 2

Preparation of (1-allylindenyl)(n-butylcyclopentadienyl)zirconium dichloride

Figure 2:
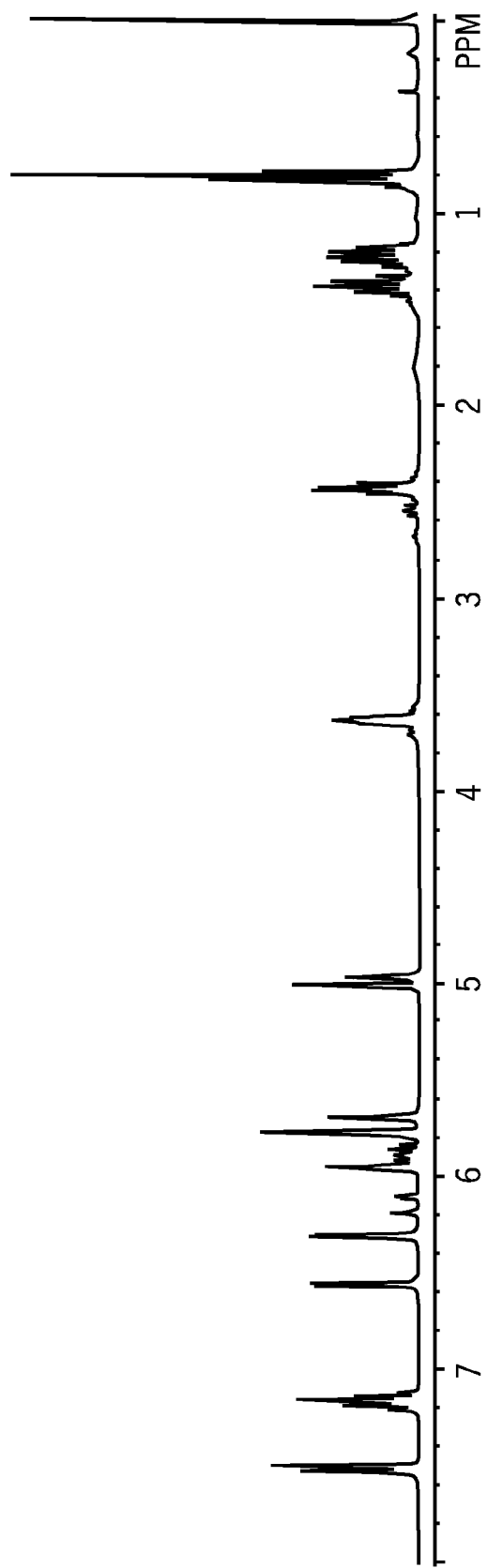
FIG. 2 is an $^1$H-NMR (CDCl$_3$) spectrum of Example Reaction 2 in accordance with embodiments of the present techniques.
Figure 3:
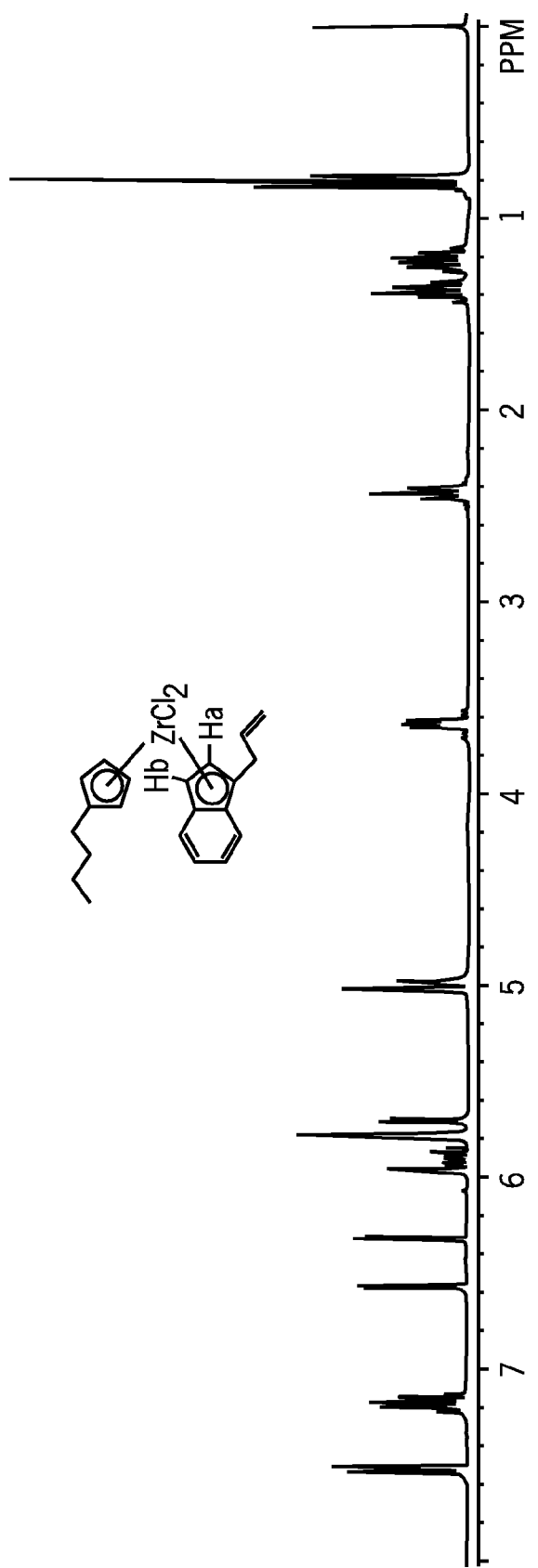
FIG. 3 is an $^1$H-NMR (CDCl$_3$) spectrum of (1-allylindenyl)(n-butylcyclopentadienyl) zirconium in accordance with embodiments of the present techniques.
Figure 4:
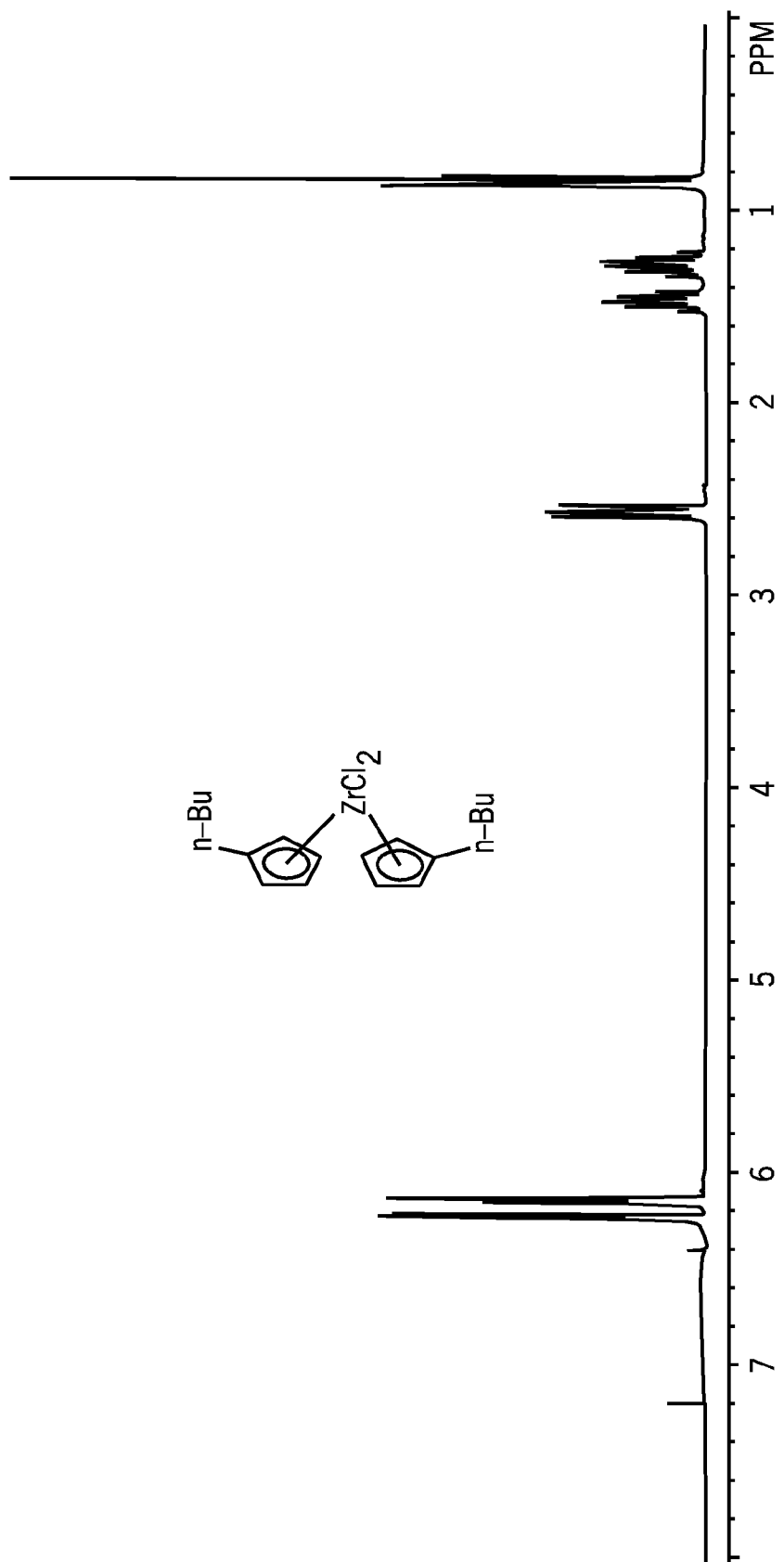
FIG. 4 is an $^1$H-NMR (CDCl$_3$) spectrum of bis(n-butylcyclopentadienyl) (zirconium dichloride) for comparative purposes.

To Tetrakis(dimethylamino)zirconium (0.52 g, 1.94 mmol) dissolved in toluene (6 mL) was added allylindene (0.31 g, 1.99 mmol) at room temperature. The mixture was stirred at room temperature overnight. To the mixture was added $Me_3SiCl$ (1 mL, 7.9 mmol) at room temperature. The mixture was stirred at room temperature overnight. Removal of the solvent gave a yellow solid (crude allylindenylzirconium trichloride). The yellow solid (crude allylindenylzirconium trichloride) was dissolved in THF (10 mL). N-BuCpLi (0.276 g, 2.15 mmol) dissolved in THF (6 mL) was added to above THF solution (allylindenylzirconium trichloride/THF solution) at 0° C. The mixture was stirred at 0° C. for 30 minutes, then warned to room temperature and stirred for another 2.5 hours. The solvent was removed. The residue was extracted with toluene (30 mL). The supernatant was separated from the solid. Removal of the solvent gave a yellow solid. The yellow solid was washed with pentane (30 mL) and then dried under vacuum. The desired compound was obtained as a pale yellow solid (0.54 g, 64% overall yield). The product was identified by $^1$H-NMR (FIG. 2).

Example 3

Preparation of $Zr\{N(CH_2CH_3)_2\}_2Cl_2(C_4H_8O)_2$ from $ZrCl_4$ and $Zr\{N(CH_2CH_3)_2\}_4$

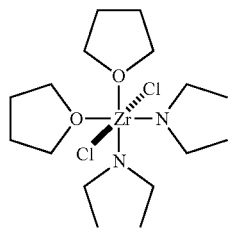

A flask was charged with zirconium tetrachloride (6.842 g, 29.36 mmol) and diethyl ether (100 mL), and was cooled in an ice water bath. A solution of zirconium tetrakis(diethylamide) (11.15 g, 29.36 mmol) in diethyl ether (30 mL) was prepared and added by cannula to the stirred suspension of zirconium tetrachloride over 1 min. Neat tetrahydrofuran (20.0 mL, 247 mmol) was added by syringe to the stirred suspension. The reaction mixture was stirred for 16 h and allowed to warm to 22 deg C. The resulting yellow suspension was concentrated to a volume of 50 mL by evaporation of solvent under vacuum. The mixture was cooled to −45 deg C for 24 h. The resulting clear supernatant solution was decanted cold from the precipitate by cannula. The precipitate was dried under vacuum for 30 min to afford the desired product as a white solid (20.15 g, 76%). A sample of this material (ca. 50 mg) was removed and dissolved in $C_6D_6$ (0.5 mL) to afford a clear pale-yellow solution. This solution was subjected to NMR analysis, which showed that the material was pure. $^1$H NMR ($C_6D_6$): δ 3.87 (m, 8H, OCH$_2$), 3.71 (q, J=7, 8H, NCH$_2$), 1.33 (m, 8H, OCH$_2$CH$_2$), 1.29 (t, J=7, 12H, NCH$_2$CH$_3$). $^{13}$C{$^1$H} NMR ($C_6D_6$): δ 72.2, 43.4, 26.2, 13.8.

Example 4

Preparation of $Zr(\eta^5$-$C_5H_4$—$\{(CH_2)_3CH_3\})\{N(CH_2CH_3)_2\}_2Cl$

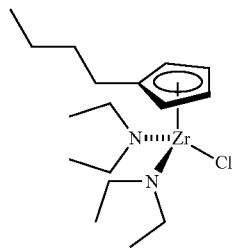

A flask was charged with $Zr\{N(CH_2CH_3)_2\}_2Cl_2(C_4H_8O)_2$ (12.31 g, 27.33 mmol) and toluene (50 mL). A solution of $Li[C_5H_4$—$\{(CH_2)_3CH_3\}]$ (3.501 g, 27.33 mmol) in tetrahydrofuran (40 mL) was prepared and added by cannula to the stirred solution of $Zr\{N(CH_2CH_3)_2\}_2Cl_2(C_4H_8O)_2$ over 1 min. The reaction mixture was stirred for 2 h and the solvent was evaporated under vacuum. The residue was suspended in heptane (10 mL) and filtered through a bed of Celite on a medium glass frit. The Celite was washed with heptane (2×20 mL), and the filtrate and washes were combined. The resulting solution was evaporated under vacuum to afford the desired product as an orange oil (10.47 g, 98%). A sample of this material (ca. 50 mg) was removed and dissolved in $C_6D_6$ (0.5 mL) to afford a clear yellow solution. This solution was subjected to NMR analysis, which showed that the material was pure. $^1$H NMR ($C_6D_6$): δ 5.99 (t, J=3, 2H, Cp), 5.96 (t, J=3, 2H, Cp), 3.37 (m, 4H, NCH$_2$), 3.16 (m, 4H, NCH$_2$), 2.65 (t, J=8, 2H, CpCH$_2$), 1.54 (p, J=8, 2H, CpCH$_2$CH$_2$), 1.30 (sextet, J=8, 2H, CpCH$_2$CH$_2$CH$_2$), 0.98 (t, J=7, 12H, NCH$_2$CH$_3$), 0.88 (t, J=8, 3H, CpCH$_2$CH$_2$CH$_2$CH$_3$). $^{13}$C{$^1$H} NMR ($C_6D_6$): δ 131.5, 111.7, 110.1, 44.2, 34.5, 30.6, 23.8, 15.9, 15.2.

Example 5

Preparation of racemic $Zr(\eta^5$-$C_5H_4$—$\{(CH_2)_3CH_3\})\{\eta^5$-$C_9H_6$-1-$(CH_2CH$=$CH_2)\}\{N(CH_2CH_3)_2\}_2$

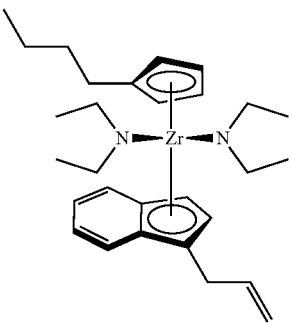

A flask was charged with $Zr(\eta^5$-$C_5H_4$—$\{(CH_2)_3CH_3\})\{N(CH_2CH_3)_2\}_2Cl$ (3.922 g, 10.00 mmol) and diethyl ether (15 mL). A solution of $Li[C_9H_6$-1-$(CH_2CH$=$CH_2)]$ (1.622 g, 10.00 mmol) in diethyl ether (15 mL) was prepared and added by cannula to the stirred solution of $Zr(\eta^5$-$C_5H_4$—$\{(CH_2)_3CH_3\})\{N(CH_2CH_3)_2\}_2Cl$ over 1 min. The reaction mixture was stirred for 30 min and the solvent was evaporated under vacuum. The residue was suspended in heptane (30 mL) and filtered through a bed of Celite on a medium glass frit. The Celite was washed with heptane (2×30 mL), and the filtrate and washes were combined. The resulting solution was evaporated under vacuum to afford the desired product as a red oil (5.050 g, 99%). A sample of this material (ca. 50 mg) was removed and dissolved in $C_6D_6$ (0.5 mL) to afford a clear orange-red solution. This solution was subjected to NMR analysis, which showed that the material was pure. $^1$H NMR ($C_6D_6$): δ 7.52 (m, 2H, Ind-$C_6$), 7.05 (m, 2H, Ind-$C_6$), 6.57 (d, J=3, 1H, Ind-$C_5$), 6.03 (m, 1H, CH=CH$_2$), 5.80 (q, J=2, 1H, Cp), 5.72 (d, J=3, 1H, Ind-$C_5$), 5.71 (q, J=2, 1H, Cp), 5.36 (q, J=2, 1H, Cp), 5.31 (q, J=2, 1H, Cp), 5.13 (dq, J=16, 1; 1H, CH=CH$_2$), 5.03 (dq, J=16, 1; 1H, CH=CH$_2$), 3.65 (m, 2H, CH$_2$CH=CH$_2$), 3.25 (m, 8H, NCH$_2$), 2.29 (m, 2H, CpCH$_2$), 1.46 (p, J=7, 2H, CpCH$_2$CH$_2$), 1.26 (sextet, J=7, 2H, CpCH$_2$CH$_2$CH$_2$), 1.06 (t, J=7, 6H, NCH$_2$CH$_3$), 0.99 (t, J=7, 6H, NCH$_2$CH$_3$), 0.94 (t, J=7, 3H, Me). $^{13}$C{$^1$H} NMR ($C_6D_6$): δ 138.0, 131.9, 131.1, 123.1, 122.1, 121.8, 121.7, 121.1, 115.1, 115.0, 112.5, 112.3, 110.1, 109.8, 89.4, 66.4, 47.0, 46.7, 35.1, 34.1, 30.1, 23.7, 16.5, 16.0, 15.8, 15.1.

Example 6

Preparation of racemic Zr($\eta^5$-C$_5$H$_4$—{(CH$_2$)$_3$CH$_3$}){$\eta^5$-C$_9$H$_6$-1-(CH$_2$CH=CH$_2$)}Cl$_2$

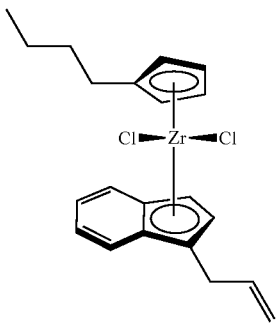

Figure 5:
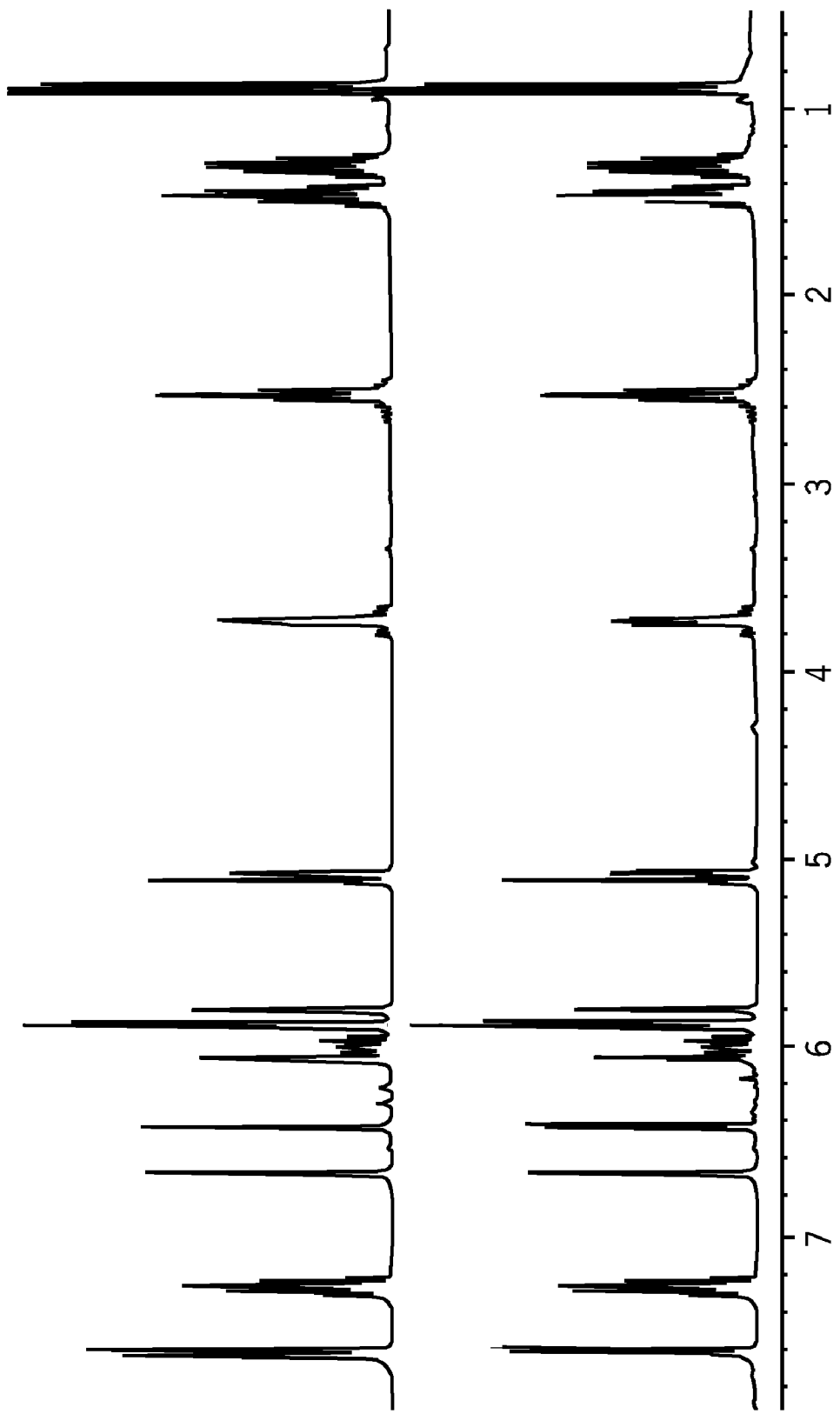
FIG. 5. is a comparison of proton NMR(CDCl$_3$) results for Example reaction 6 in accordance with embodiments of the present techniques.

A flask was charged with racemic Zr($\eta^5$-C$_5$H$_4$—{(CH$_2$)$_3$CH$_2$)$_3$CH$_3$}){$\eta^5$-C$_9$H$_6$-1-(CH$_2$CH=CH$_2$)}{N(CH$_2$CH$_3$)$_2$}$_2$ (5.000 g, 9.768 mmol) and diethyl ether (50 mL), and was cooled in an ice water bath. A solution of HCl in diethyl ether (10 mL, 2.0 M, 20 mmol) was added by syringe to the stirred solution of racemic Zr($\eta_5$-C$_5$H$_4$-{(CH$_2$)$_3$CH$_3$}){$\eta^5$-C$_9$H$_6$-1-(CH$_2$CH=CH$_2$)}{N(CH$_2$CH$_3$)$_2$}$_2$ over 1 min. The mixture was stirred for 15 min, and the bath was removed. The mixture was stirred for 30 min and diethyl ether (50 mL) was added by cannula. The resulting yellow slurry was filtered on a medium glass frit. The filtered precipitate was dried under vacuum to afford the desired product as pale-yellow solid (1.549 g, 35%). A sample of this material (ca. 50 mg) was removed and dissolved in CDCl$_3$ (0.5 mL) to afford a clear yellow solution. This solution was subjected to NMR analysis, which showed that the material was pure desired compound based on comparison with previously reported data (FIG. 5).

While the techniques disclosed above may be susceptible to various modifications and alternative forms, specific embodiments have been shown by way of example in the drawings. However, it should be understood that the techniques are not intended to be limited to the particular forms disclosed. Rather, the techniques encompass all modifications, equivalents and alternatives falling within the spirit and scope of the techniques as defined by the following appended claims.

What is claimed is:

1. A method for making a catalyst from a catalyst precursor, comprising: reacting a catalyst precursor with an $\eta$-5 type ligand complex to form a catalyst, wherein:

the catalyst precursor has a general structure of:

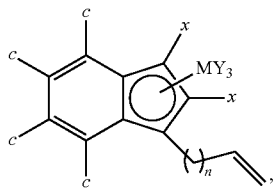

wherein:

M is Zr or Hf;

each x is independently selected from a hydrogen, alkyl, branched alkyl, cycloalkyl, aryl, or alkenyl group having from 2 to 20 carbons;

n is 1, 2, 3, 4, 5, 6, 7, or 8;

each c is independently selected from a hydrogen, alkyl, branched alkyl, cycloalkyl, aryl, or alkenyl group having from 2 to 20 carbons, or at least one c is joined with another c to form a ring;

each Y is independently a halide or NR$_2$, wherein each R is independently a hydrocarbyl group having from 1 to 5 carbons;

the $\eta$-5 type ligand metal complex comprises a cyclopentadienyl, a substituted cyclopentadienyl, an indenyl, a substituted indenyl, a fluorenyl, or a substituted fluorenyl complexed with a group I or a group II metal; and the catalyst has a general structure of:

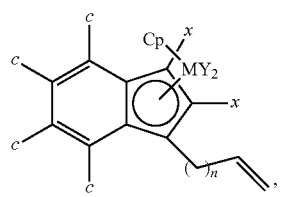

wherein Cp is an $\eta$-5 type ligand comprising a cyclopentadienyl, a substituted cyclopentadienyl, an indenyl, a substituted indenyl, a fluorenyl, or a substituted fluorenyl.

2. The method of claim 1, wherein the catalyst has a general structure of:

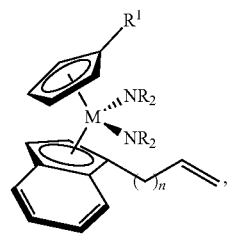

wherein R$^1$ is a hydrocarbyl group having from 1 to 10 carbons.

3. The method of claim 1, wherein the catalyst has a structure of:

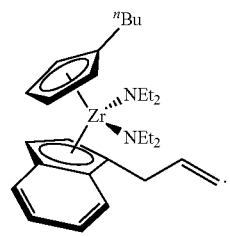

4. The method of claim 1, wherein the catalyst has a general structure of:

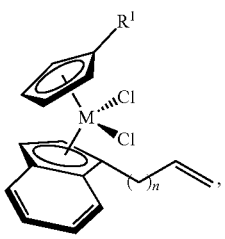

wherein $R^1$ is a hydrocarbyl group having from 1 to 10 carbons.

5. The method of claim 1, wherein the catalyst has a structure of:

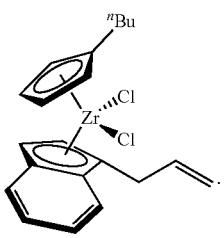

6. The method of claim 1, wherein M is Hf.
7. The method of claim 1, wherein M is Zr.
8. The method of claim 1, wherein Y is Cl.
9. The method of claim 1, wherein Y is $NR_2$.
10. The method of claim 1, wherein at least one c is conjoined with another c to form a ring.
11. A method for making a catalyst from a catalyst precursor, comprising:
reacting a catalyst precursor with an η-5 type ligand complex to form a catalyst, wherein:
the catalyst precursor has a general structure of:

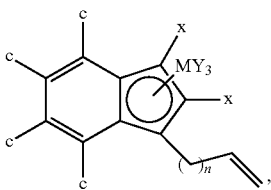

wherein:
M is Ti, Zr, or Hf;
each x is independently selected from a hydrogen, alkyl, branched alkyl, cycloalkyl, aryl, or alkenyl group having from 2 to 20 carbons;
n is 1, 2, 3, 4, 5, 6, 7, or 8;
each c is independently selected from a hydrogen, alkyl, branched alkyl, cycloalkyl, aryl, or alkenyl group having from 2 to 20 carbons, or at least one c is joined with another c to form a ring;
each Y is independently a halide or $NR_2$, wherein each R is independently a hydrocarbyl group having from 1 to 5 carbons;
at least one Y of the catalyst precursor is $NR_2$;
the η-5 type ligand metal complex comprises a cyclopentadienyl, a substituted cyclopentadienyl, an indenyl, a substituted indenyl, a fluorenyl, or a substituted fluorenyl complexed with a group I or a group II metal; and
the catalyst has a general structure of:

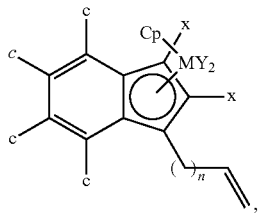

wherein Cp is an η-5 type ligand comprising a cyclopentadienyl, a substituted cyclopentadienyl, an indenyl, a substituted indenyl, a fluorenyl, or a substituted fluorenyl.

12. The method of claim 11, wherein the catalyst has a general structure of:

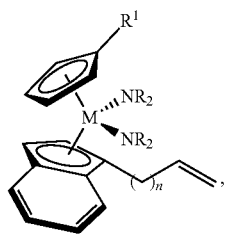

wherein $R^1$ is a hydrocarbyl group having from 1 to 10 carbons.

13. The method of claim 11, wherein the catalyst has a general structure of:

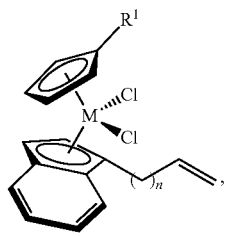

wherein $R^1$ is a hydrocarbyl group having from 1 to 10 carbons.

14. The method of claim 11, wherein M is Ti.

15. A method for making a catalyst from a catalyst precursor, comprising:

reacting a catalyst precursor with an η-5 type ligand complex to form a catalyst, wherein:

the catalyst precursor has a general structure of:

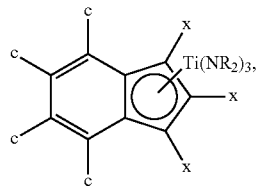

wherein:

each x is independently selected from a hydrogen, alkyl, branched alkyl, cycloalkyl, aryl, or alkenyl group having from 2 to 20 carbons;

each c is independently selected from a hydrogen, alkyl, branched alkyl, cycloalkyl, aryl, or alkenyl group having from 2 to 20 carbons, or at least one c is joined with another c to form a ring;

the η-5 type ligand metal complex comprises a cyclopentadienyl, a substituted cyclopentadienyl, an indenyl, a substituted indenyl, a fluorenyl, or a substituted fluorenyl complexed with a group I or a group II metal; and the catalyst has a general structure of:

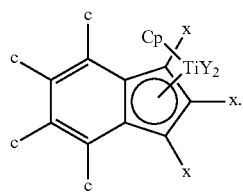

wherein:

each Y is independently a halide or $NR_2$, wherein each R is independently a hydrocarbyl group having from 1 to 5 carbons; and Cp is an η-5 type ligand comprising a cyclopentadienyl, a substituted cyclopentadienyl, an indenyl, a substituted indenyl, a fluorenyl, or a substituted fluorenyl.

16. The method of claim 15, wherein at least one x is a terminal alkene.

17. The method of claim 15, wherein the catalyst has a general structure of:

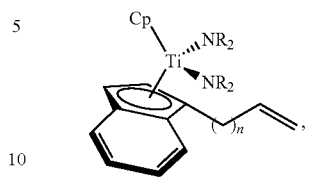

wherein n is 1, 2, 3, 4, 5, 6, 7, or 8.

18. The method of claim 15, wherein the catalyst has a general structure of:

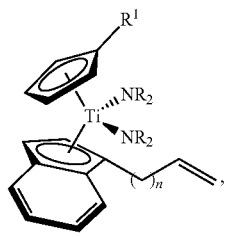

wherein:

$R^1$ is a hydrocarbyl group having from 1 to 10 carbons; and n is 1, 2, 3, 4, 5, 6, 7, or 8.

19. The method of claim 15, wherein the catalyst has a general structure of:

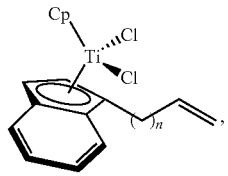

wherein n is 1, 2, 3, 4, 5, 6, 7, or 8.

20. The method of claim 15, wherein the catalyst has a general structure of:

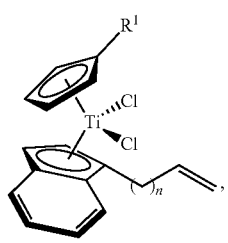

wherein:

$R^1$ is a hydrocarbyl group having from 1 to 10 carbons; and n is 1, 2, 3, 4, 5, 6, 7, or 8.

* * * * *